(12) United States Patent
Toth

(10) Patent No.: US 7,789,664 B1
(45) Date of Patent: Sep. 7, 2010

(54) CAPTURE OF A PLANNED VERTICAL DIMENSION OF OCCLUSION TO FACILITATE SIMULTANEOUS RESTORATION OF BOTH MAXILLARY AND MANDIBULAR ARCHES USING IMPLANTS

(76) Inventor: Richard W. Toth, 3002 Fox Mill Rd., Oakton, VA (US) 22124

( * ) Notice: Subject to any disclaimer, the term of this patent is extended or adjusted under 35 U.S.C. 154(b) by 578 days.

(21) Appl. No.: 11/707,291

(22) Filed: Feb. 16, 2007

(51) Int. Cl.
*A61C 9/00* (2006.01)

(52) U.S. Cl. ..................... 433/214; 433/213

(58) Field of Classification Search ............. 433/213, 433/214, 172
See application file for complete search history.

(56) References Cited

U.S. PATENT DOCUMENTS 7,452,207 B2 * 11/2008 Miller et al. ............. 433/71

* cited by examiner

Primary Examiner—Cris L Rodriguez
Assistant Examiner—Eric Rosen
(74) Attorney, Agent, or Firm—David L. Banner

(57) ABSTRACT

Apparatus and method enabling implant supported dental prostheses to be fabricated for reconstruction of both maxillary and mandibular arches from a procedure requiring only one surgery. At least three pairs of reference points in the maxillary arch and in the mandibular arch are connected by adjustable members which are subsequently fixed in length and in mutual orientation to enable necessary impressions and casts to be made. The adjustable members engage anchoring members such as ball headed screws which are fixed to the maxillary and mandibular anatomy. Subsequently fabricated mechanical models of the patient anatomy, such as impressions and casts, capture critical geometric relationships from the adjustable members and their associated anchoring members, thereby enabling both maxillary and mandibular implant mountable prostheses to be fabricated from information gathered during only one surgical session.

14 Claims, 8 Drawing Sheets

| Step | Conventional Practice | Present Invention |
|---|---|---|
| 1 | Prosthodontic evaluation | Prosthodontic evaluation |
| 2 | Surgical evaluation | Surgical evaluation |
| 3 | Diagnostic casts made | Diagnostic casts made |
| 4 | First arch indexes made (guides, templates, etc.) | Indexes made (guides, templates, etc.) for both arches |
| 5 | First arch surgery (implants) and impression | Both arch surgery (implants), bite registration work, employing novel apparatus and impressions |
| 6 | First arch bite registration lab device, made at laboratory | Make and deliver all prostheses for subsequent installation |
| 7 | First arch bite registration device used clinically | Healing period |
| 8 | Make and deliver first arch prostheses | New impressions, make and deliver definitive prostheses (for both arches) |
| 9 | Healing period | |
| 10 | Second arch indexes made (guides, templates, etc.) | |
| 11 | Second arch surgery (implants) and impression | |
| 12 | Second arch bite registration lab device made in laboratory | |
| 13 | Second arch bite registration device used clinically | |
| 14 | Make and deliver second arch prostheses | |
| 15 | Healing period | |
| 16 | New impressions, make and deliver definitive prostheses for both arches | |

Fig. 12

CAPTURE OF A PLANNED VERTICAL DIMENSION OF OCCLUSION TO FACILITATE SIMULTANEOUS RESTORATION OF BOTH MAXILLARY AND MANDIBULAR ARCHES USING IMPLANTS

BACKGROUND OF THE INVENTION

1. Field of the Invention

The present invention relates to method and apparatus for enabling restoration of all or almost all teeth of both dental arches of either an edentulous or a dentate patient, using implants to anchor restorative prostheses, in a procedure requiring only one surgical session.

2. Description of the Prior Art

It is occasionally required to restore all or almost all maxillary and mandibular teeth of a patient. In practices of the prior art, bridgework and other restorative devices may be anchored to bone tissue by osseointegrated implants. Such extensive procedures have traditionally been done in at least two major stages, one arch being restored first and the second arch being subsequently restored. Each arch is restored by indexing occlusal and other relationships based on using the opposing arch for benchmarks or reference points.

Procedures using such above two stage approaches have succeeded. However, these procedures entail significant disadvantages. For example, a relatively large number of surgeries and office visits are required to get a patient to the point that functional prostheses for both arches can be delivered to the patient and installed. Also, the total time window which elapses between the first steps of the procedure and the point that functional prostheses can be delivered may be extended.

In the specific situation wherein a patient is completely edentulous, it is possible to use computer generated surgical guides and prostheses to accomplish the goal of restoration requiring only one surgery. However, this computerized approach fails when teeth are present because of the necessity of fabricating and actually placing in the mouth a removable prosthesis, which is obstructed by existing teeth.

There exists a need in the prior art for an implant based restorative procedure which reduces the number of surgeries and office visits in two arch dental reconstructions, and particularly in cases wherein at least one tooth or denture is present at the outset.

SUMMARY OF THE INVENTION

The present invention addresses the above need by setting forth an approach in which implants for both maxillary and mandibular arches are implanted in a single surgery.

This reduction from the several surgeries of the prior art to one surgery is based on a unique procedure for capturing a maxillary and mandibular relation for assembly of a master model. The present invention is described herein as enabling simultaneous reconstruction of maxillary and mandibular arches. This description is only a semantic convenience introduced for the purpose of emphasizing that the necessary work to produce prostheses for both arches can be based on only one surgery, as opposed to at least two surgical sessions required in the prior art. There is no necessity of literally forming prostheses simultaneously.

As employed herein, a single surgical session will be understood to mean that the patient comes to the premises of the surgery once, at least for the initial surgery. The patient does not leave to go home and return to the surgical premises, or undertake any activity (e.g., shopping, visiting, conducting financial transactions, etc.) unrelated to the dental surgery. However, the surgical session may be briefly interrupted, for example to allow the patient or the dental practitioner to use toilet facilities, to engage in an important telephone call or conversation, or for other brief interruptions. Surgery may be temporarily suspended for surgical purposes, such as for example to remove unnecessary implements and material, or to make available new implements and materials, to conduct brief consultations with others who may be onsite or remote therefrom. Such brief interruptions are not deemed to have created two surgical sessions from one. The single surgical session will ordinarily be limited to normal business hours of one day.

The novel approach is based on first generating an "as-is" geometric assembly or mechanical index which captures certain anatomical relationships of the anatomy of the patient's mouth in its original state. This "as-as" index encompasses both maxillary and mandibular arches and enables the three dimensional construction of an "as-desired" geometric assembly or mechanical model which reflects just-placed dental. The first or "as-is" assembly serves to orient the maxillary arch to the mandibular arch for subsequently fabricated models and prosthesis position adjustments. The second or "as-desired" model inherits accuracy from the first assembly and permits final fabrication and adjustment of the prostheses. It is important to note that the first, "as-is" assembly captures and mutually orients both maxillary and also mandibular anatomy that enables simultaneous fabrication of upper and lower prostheses.

This novel procedure starts by establishing typically three reference points at the maxillary arch and three additional reference points at the mandibular arch. The reference points are provided by temporarily installing (i.e., only for the duration of the surgical session) six ball headed screws or equivalents in the patient's mouth. Three screws are located in the maxillary arch and three screws are located in the mandibular arch. Each upper or maxillary ball headed screw is associated with one lower or mandibular ball headed screw, thereby defining three associated pairs of ball-headed screws. Each associated pair of ball headed screws is then connected by an adjustable member having two ball sockets adapted to receive the ball heads of the screws. These ball sockets enable the adjustable member to engage each of the associated pair of ball headed screws. One adjustable member is connected to each of the three associated pairs of ball headed screws. By way of analogy, these adjustable members may be envisioned as turnbuckles which are adjustable as to length, and which engage an anchor at each end. In this analogy, the balls of the ball headed screws serve as the so-called anchors.

After the three adjustable members are each anchored to respective associated pairs of ball-headed screws, impression material is then placed against the three adjustable members. The adjustable members are thereby entrapped or indexed in the resultant impression. Thus, the distance spanning each pair of upper and lower reference points, and also three dimensional relationships of these three members, are all captured in the removable "as-is" mechanical assembly formed by the impression material. This "as-is" mechanical assembly is subsequently used to maintain maxillary to mandibular orientation throughout the remainder of the novel procedure. Otherwise stated, the six total reference points defined by the ball-headed screws are fixed by the assembly in three dimensions such that not only the vertical dimension of occlusion (VDO) is captured, but also the three dimensional locations of the six points are captured. The impression also captures the pre-surgical plane of occlusion and position of any teeth or dentures.

In a subsequent step, "as-desired" impressions and casts are fabricated to include analogs of the ball headed screws as well as dental implants which are typically installed during the single surgical session. The "as-desired" impressions and casts permit fabrication of suitable prostheses, both upper and lower, which will reflect the VDO and other necessary relationships. The resultant prostheses are based on established implant characteristics, and therefore will be suitable for installation without requiring one arch to be reconstructed first and the second to be reconstructed relying on the first arch for geometric inputs.

It will be appreciated that impressions reflecting all implants and all critical indexing or measurement relationships are captured by this novel process. Surgery is now complete, with all necessary maxillary and mandibular implants in place. It remains for a suitable fixed bridge prosthesis or prostheses to be fabricated in a laboratory using any suitable techniques known to those of skill in the art and, once fabricated, installed in the patient's mouth. As employed herein, "fixed" refers to securement by a method not intended to be removed by the patient to distinguish such securements from patient removable dentures or other removable oral appliances. Fixed prosthesis are typically crewed in place and can not be removed by the patient. Screws, cement and other methods of attachment which are normally serviced by a person other than the patient are examples of fixed attachment.

FIG. 12 is a table summarizing significant steps during the surgery and healing phase of treatment of conventional two-arch reconstructions of the prior art, and comparing these to comparable steps of the novel method of two-arch reconstruction. The first step, common to both conventional practice and to the present invention, is that of conducting an evaluation of the patient. In some cases, this may require at least one visit to a prosthodontist and further visits to an oral surgeon in a second step. The third step, also common to both approaches, is that of making and mounting diagnostic casts on the articulator to aid fabrication of templates and surgical guides.

At this point, the two approaches diverge. In conventional practice, the fourth step is that of preparing for treatment of only the maxillary arch. It is also possible that the mandibular arch may be the subject of this step. By contrast, in the present invention, templates, indexes, and surgical guides for both arches are made in the fourth step, combining the procedures for both arches to be treated simultaneously rather than one at a time as the prior art requires.

In conventional, prior art practice, the fifth step is to perform maxillary surgery. The fifth step in the novel method is to perform surgery for both arches at the same time (i.e., during the same surgical session). Note that the novel assembly which incorporates the connector bars enables this. No corresponding device exists in the prior art.

In the sixth step of the conventional method, bite registration, sometimes referred to as the jaw relation record, is captured. At a corresponding point in the novel method, bite registration has already been accomplished during the fifth step. Consequently, bridgework or functional temporary prostheses for both arches may be made and delivered for installation.

At this point, surgical steps in the novel method are complete. But in conventional practice, about seven significant additional steps remain. Of course, depending upon specific procedures as undertaken by different practitioners, definition of surgical steps is somewhat subjective. For example, some practitioners will, for either practical or even semantic purposes, break down one step into several steps. Therefore, the seven steps referred to herein will be described functionally, it being understood that the actual number of steps could be regarded as either more or fewer than seven depending upon the individual practitioner.

These seven significant steps typically include capturing the VDO with an index made after and separate from the surgery, making and delivering the maxillary prosthesis, allowing an appropriate healing period, and then treating the remaining arch as though the latter were a separate or new case. It must be borne in mind that additional surgeries and healing periods are also required in conventional practice. The remaining steps in conventional practice typically include making new impressions; making indexes; conducting mandibular surgery; making mandibular measurements, using impressions; and delivering functional temporary prostheses.

Obviously, great progress is made in a brief period of time using the novel method. The applicant estimates that using his novel two-arch approach save at least one-two months compared to methods of the prior art in delivering definitive or non-temporary prostheses for both arches. This additional time is a burden shouldered by the patient in conventional practice, but eliminated by the novel method. It is also contemplated that actual office time savings to the prosthodontist and surgeon enables them to increase professional earnings and potentially passing a discount or savings over the conventional method charges on to the patient.

Benefits to the patient, beyond reducing the number of major surgeries from two to one and reducing the time window by at least one to two months, include eliminating post-operative measurements when a patient is typically numb and bleeding immediately following surgery; and reducing the number of total trips or visits to offices of dental professionals from about thirteen to about seven.

It is, therefore, an object of the invention to provide a surgical prosthetic method for simultaneous two-arch reconstruction, which surgical method extends from the first surgical step to the point that functional prostheses can be delivered for installation, which surgical method requires only one surgery and one subsequent surgical appointment to deliver the prostheses to both arches.

It is also an object of the invention to provide apparatus enabling a single surgery to enable simultaneous delivery of all prostheses for a two-arch reconstruction.

Another object of the invention is to reduce the clinical time demanded of highly skilled dental professionals in a two-arch reconstruction, and to reduce the time window during such a reconstruction.

It is an object of the invention to provide improved elements and arrangements thereof by apparatus for the purposes described which is relatively inexpensive, dependable, and fully effective in accomplishing its intended purposes.

These and other objects of the present invention will become readily apparent upon further review of the following specification and drawings.

BRIEF DESCRIPTION OF THE DRAWINGS

Various objects, features, and attendant advantages of the present invention will become more fully appreciated as the same becomes better understood when considered in conjunction with the accompanying drawings, in which like reference characters designate the same or similar parts throughout the several views, and wherein:

FIG. 12 is a table comparing the number of steps required in the novel procedure to that of a comparable prior art procedure.

DETAILED DESCRIPTION OF THE PREFERRED EMBODIMENTS

The present invention provides a method of and apparatus for capturing the three dimensional orientation of the jaws of a patient at a planned vertical dimension of occlusion (VDO), to enable fixed restoration of both dental arches simultaneously in one surgery. This requires installing geometric apparatus at the beginning of the single surgery in the mouth of the patient. The geometric apparatus captures and preserves in fixed form sufficient geometric relationships of the mouth to enable a dental professional to fabricate dental prostheses to an accurate reproduction of an appropriate occlusal plane. This procedure requires three reference points at the maxillary arch and three reference points at the mandibular arch. The six total reference points are fixed by the assembly in three dimensions such that not only the VDO is captured, but the exact positions of the six points in three dimensional space are captured.

Figure 1:
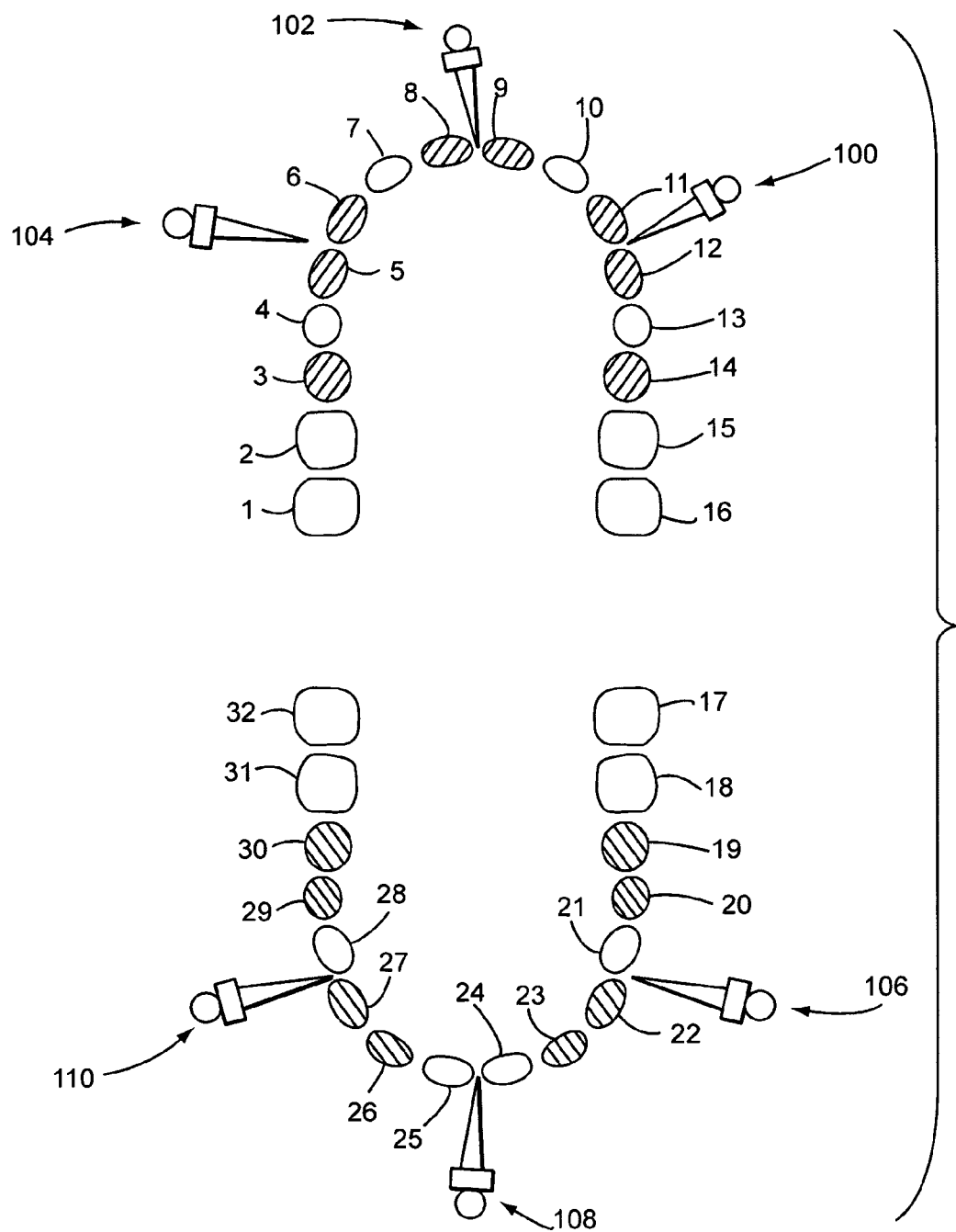
FIG. 1 is a schematic, diagrammatic representation of the anatomy of the mouth of a hypothetical dental patient showing some of the apparatus of the present invention.

FIG. 1 is a schematic representation of the maxillary and mandibular arches of a hypothetical patient who is to have all remaining teeth extracted. In FIG. 1, reference numerals 1 through 32 correlate to the standard tooth site identification convention employed generally by dental professionals in the United States. Implant sites are indicated by cross hatching. In the example of FIG. 1, implant sites include maxillary tooth positions 3, 5, 6, 8, 9, 11, 12, and 14. Remaining tooth positions 1, 2, 4, 7, 10, 13, 15, and 16 need not be disturbed. In many cases, there may possibly be no teeth at the remaining tooth positions. Mandibular implant sites include tooth positions 19, 20, 22, 23, 26, 27, 29, and 30. As with the maxillary sites, and other than extractions, remaining tooth positions 17, 18, 21, 24, 25, 28, 31, and 32 are not to be disturbed.

The first step of the inventive method is the fabrication of an index which will serve as the basis for future mutual orientation of models or casts. In a subsequent step, a two-piece impression is formed, to enable forming the models or casts. It should be clarified at this point that impressions, such as that forming part of the impression index 150, are "negatives" of the three dimensional objects the configuration of which they capture. This follows since impressions are formed by packing moldable material around an existing object. By contrast, casts and models, the latter two terms being interchangeable herein, are "positives" of the three dimensional objects they reproduce. Casts and models are made by packing impressions with moldable material, such as dental stone, which moldable material then forms a nearly exact reproduction of the three dimensional objects characteristics of which were originally captured by impressions.

The index captures and preserves the aforementioned reference points. These reference points are established by pins that are temporarily driven or otherwise inserted into bone tissue. This is done in the same surgical session as the setting of implants. As setting of reference pins and of implants are the only tissue invasive aspects of the procedure, it follows that only one surgical session is necessary.

Figure 2:
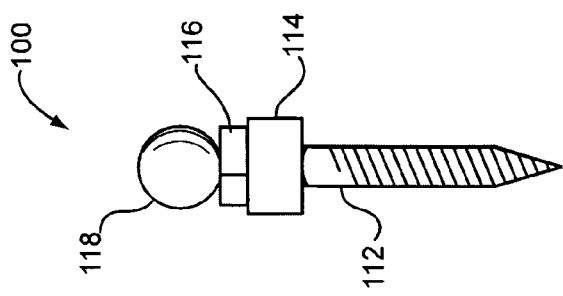
FIG. 2 is an enlarged, side elevational view of an embodiment of a ball-headed screw component of the apparatus of the present invention, as seen in FIG. 1.

Reference pins in the form of three ball headed screws 100, 102, 104 are installed in maxillary bone tissue as will be described hereinafter. Three corresponding ball headed screws 106, 108, 110 are subsequently installed in mandibular bone tissue in locations shown representatively in FIG. 1. FIG. 2 presents a detailed view of ball headed screw 100, which is representative of remaining ball headed screws 102, 104, 106, 108, 110. Screw 100 has a pointed threaded shaft 112, a base 114 which will cooperate with a subsequently fabricated surgical guide (not shown), a hexagonal section 116 for turning screw 100 into bone tissue, and a spherical head or ball 118. Ball headed screws 100, 102, 104, 106, 108, 110 are threaded or driven into bone tissue in suitable locations which preferably but not necessarily establish pairs of substantially vertically aligned screws 100 and 106, 102 and 108, and 104 and 110. Screws 100, 102, 104, 106, 108, 110 are located for ease of manipulation and solidity of the installation. It will be appreciated that screws 100 . . . 110 serve as reference markers in sufficient number and in appropriate locations from which to capture the VDO for the patient. The preferred sites for screws 100, 102, 104, 106, 108, 110 are any locations which have bone tissue of sufficient strength to support screws 100, 102, 104, 106, 108, 110. However, it is important that the chosen locations for pins 100 . . . 110 neither interfere with implant placement, nor disturb teeth and prostheses which are to remain.

It should be mentioned at this point that references to orientations such as "upper", "lower", "vertical", and the like, are based on that orientation which exists when the patient is in a standing position, with his or her neck generally aligned with the backbone, and looking straight ahead. Just as "upper jaw" is intuitively regarded as the maxillary jaw, so will orientational terms apply to the standing position. Obviously, there is no "upper jaw" when a patient is lying prone in the practitioner's chair. Where orientation changes with, for example, whether the maxillary or mandibular anatomy is being discussed, then the referenced drawing figures will determine orientation. For example, the upper portion of ball headed screw 100 (or of any of screws 100, 102, 104, 106, 108, 110) will be that which is the upper portion as depicted in FIG. 2, regardless of actual orientation of a screw 100, 102, 104, 106, 108, 110.

Figure 3:
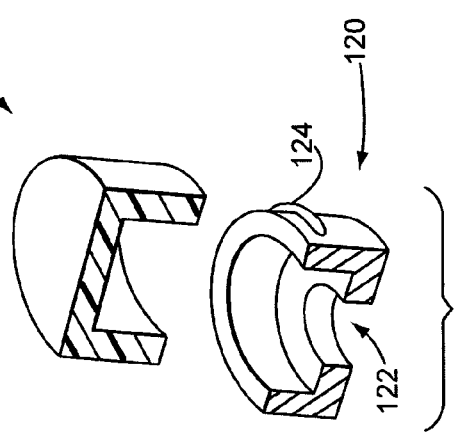
FIG. 3 is a partly cross sectional, exploded perspective view of cup and cap components which are to be assembled to the apparatus of FIG. 2.

Turning briefly to FIG. 3, the upper or midshaft portion of each screw 100, 102, 104, 106, 108, 110 is enclosed prior to installation to prevent contamination by materials used in model and impression making. A cup or seat 120 surrounds the head of each screw 100, 102, 104, 106, 108, 110 in close cooperation therewith. A central opening 122 in seat 120 allows passage of shaft 112. Seat 120 has one or more external ribs 124 or other texturizing structure at its outer surface. Rib 124 or analogous structures engage a hardenable material such as a light cured acrylic material which will subsequently be applied to form the impression in any conventional manner after implant placement. A hand made or computer made surgical guide, not shown, may be utilized to enable appropriate placement of screws 100, 102, 104, 106, 108, 110. The surgical guide may be dedicated to screw placement, or may be the same surgical guide used for implant installation. In some cases, although not preferred, no surgical guide will be utilized.

Seat 120 becomes a permanent part of the impression and will seat a screw 100, 102, 104, 106, 108, 110 or an analog thereof within the impression in a subsequent operation. A removable sleeve or cap 126 completes enclosure of the upper portion of the screw. Cap 126 serves as a protective barrier to prevent, impression material from fouling ball 118 of the screws 100, 102, 104, 106, 108, 110 in a subsequent impression forming operation. Caps 126 are discarded after the impression is made.

Once installed with their threaded shafts 112 engaging bone tissue, balls 118 of screws 100, 102, 104, 106, 108, 110 project outwardly from their respective arches. One ball 118 from the maxillary arch is then connected to a corresponding ball 118 of the mandibular arch by a connector bar which is placed in spanning relationship between one maxillary reference marker (e.g., and a corresponding first mandibular reference marker.

Figure 4:
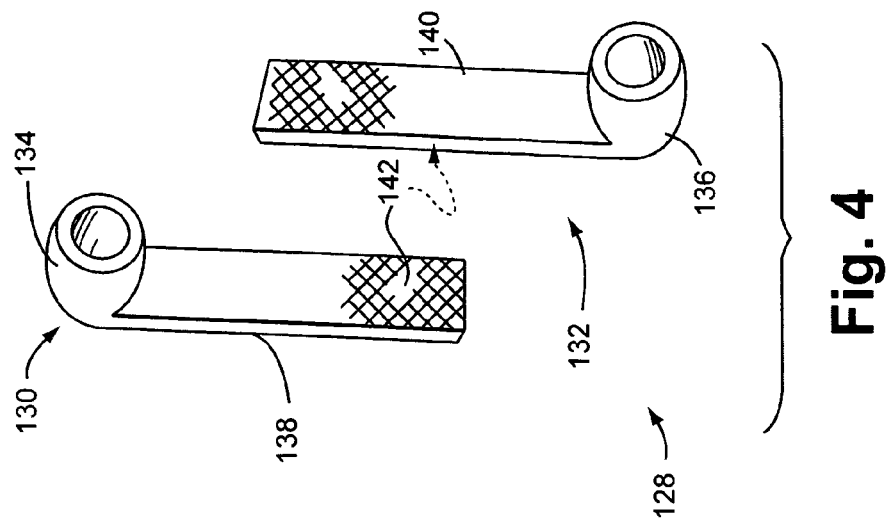
FIG. 4 is an exploded perspective view connector bar components prior to joining which are subsequently assembled to the apparatus seen in FIG. 1.

Referring now to FIG. 4, connector bars 128 are initially formed in two complementary, elongated sections or pieces 130, 132, each having one socket 134, 136, respectively. Sockets 134, 136 are disposed to resiliently engage an exposed ball 118 of a screw 100, 102, 104, 106, 108, 110. A straight section 138, 140 (or in an alternative embodiment, an angled corresponding section) projects from each socket 134, 136. One upper exposed ball 118 and one corresponding lower exposed ball 118 are then joined by connector bar 128. After resiliently and releasably engaging the balls 118, straight sections 138, 140 (or angled sections) of connector bar 128 are joined together to capture the ball-to-ball dimension. It is presently preferred to use a light cured acrylic material to join the members, although other methods such as mechanical fasteners could be employed. Each straight section 138 or 140 (or angled section) has texturing 142 to secure adhesion of luting material 133.

Figure 5:
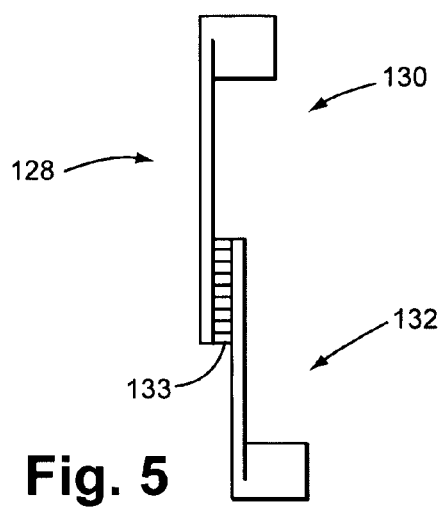
FIG. 5 is a side elevational view of the components of FIG. 4, shown joined.
Figure 7:
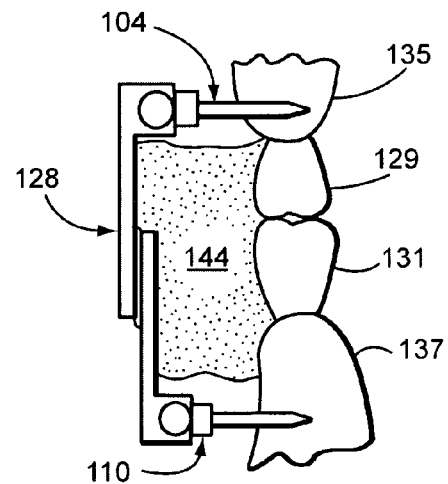
FIG. 7 is a side elevational view, shown partly in cross section, of the impression index of FIG. 6, shown in a deployed condition installed in the mouth of a patient.

FIG. 5 shows a connector bar 128 after complementary sections 130, 132 are joined. FIG. 7, which will be further described hereinafter, shows a joined connector bar 128 in its operative position spanning ball headed screws 104, 110 which have been driven into maxillary and mandibular bone tissue, respectively with the patient's jaws closed.

Figure 6:
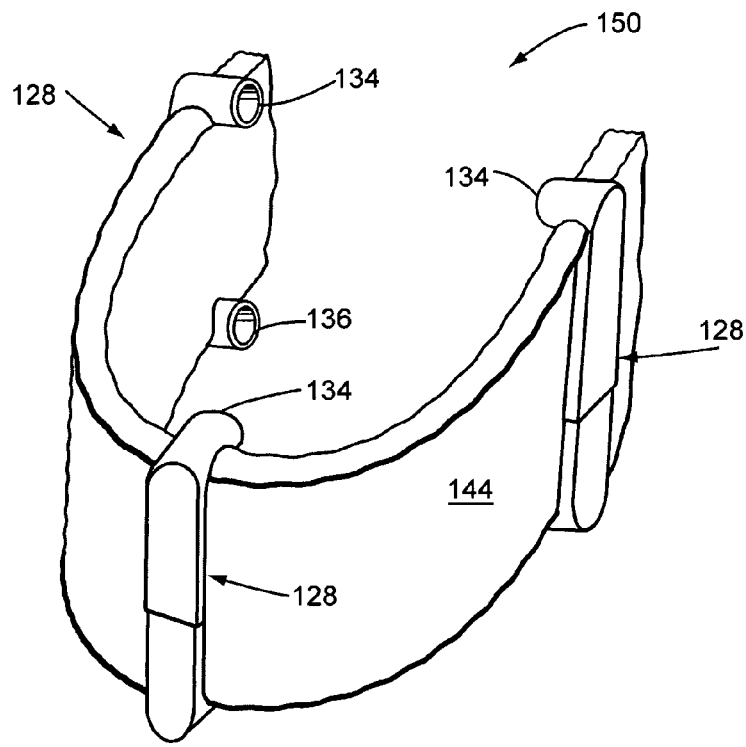
FIG. 6 is a diagrammatic perspective view of one embodiment of an impression index of the apparatus of the invention.

The step of installing and unifying the complementary sections 130, 132 of connector bar 128 is repeated typically two more times so that three paired connector bars 128 join three associated pairs of screws 100/106; 102/108; and 104/110. Referring now also to FIG. 6, an indexing impression 150 is then made using a dental impression material such as polyvinyl siloxane or another suitable material known to those of skill in the art to capture the three dimensional relationship of connector bars 128, teeth and/or dentures, and the occlusal plane. This impression index 150, which has captured and integrated the three now united connector bars 128 and their positions relative to one another, is then removed from the patient's mount and set aside for subsequent use in the laboratory. It is important to note that this impression index 150 has captured the "as-is" pre-surgical relationships of the jaws, and will be used to establish the "as-desired" relationships of the post-surgical models made after implant placement.

FIG. 7 shows how impression index 150 is made. With associated pairs of ball headed screws (only ball headed screws 104, 110 being visible in FIG. 7) (installed in bone tissue of the patient's jaws, impression material 144 is packed into place in the mouth, where it engages a connector bar 128 and also has captured anatomical details of teeth 129, 131 (natural, denture or other) and of gums 135, 137. It will be recognized that while only ball headed screws 104, 110 are shown in FIG. 7, at least three pairs of reference are required by the inventive method. Impression index 150 is used subsequently to relate maxillary and mandibular casts when such casts are fabricated. Impression index 150 is removed and set aside.

Once impression index 150 is removed from the patient's mouth, conventional dental implants, such as implant 152 (FIG. 8) are then implanted in conventional manner, preferably using a conventional or computer generated surgical guide (neither shown). Ball headed screws 100 . . . 110 are left in place as they have been located so as not to interfere with implant placement.

Two complementary impressions (one maxillary and the other mandibular) reflecting the newly installed dental implants and ball headed screws 100, 102, 104, 106, 108, 110, with balls or spherical heads 118 exposed, are then made using a suitable dental impression material. One of these complementary impressions captures impressions of maxillary implants, of three maxillary ball headed screws (e.g., 100, 102, 104, 106, 108, 110), seats or sleeves 120 (FIG. 3), and the desired maxillary arch anatomy. As will be recognized by those skilled in the art, face bow measurements may be taken with the impression still in place as needed.

Figure 8:
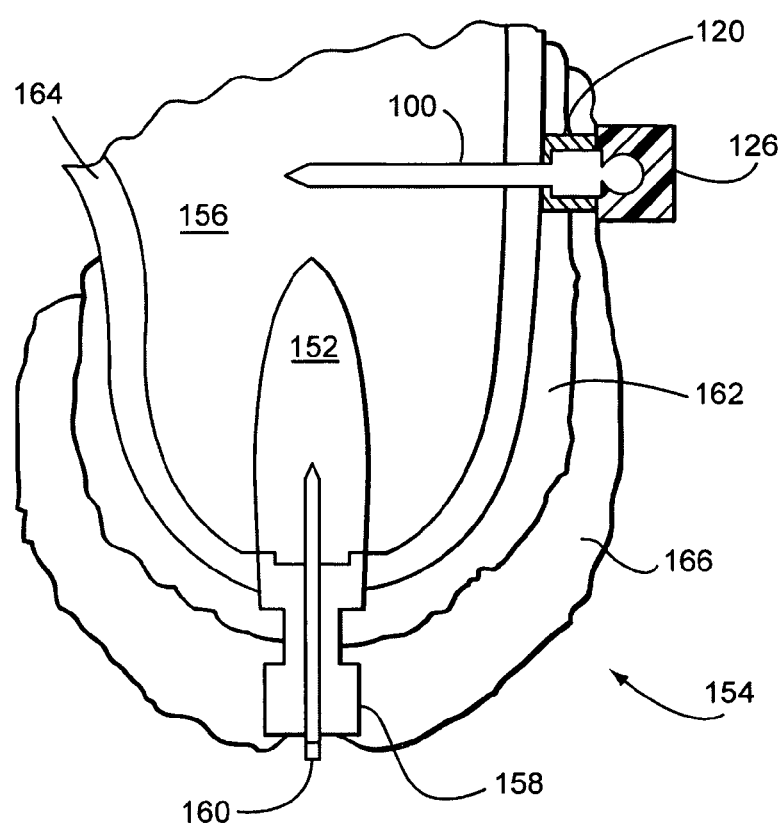
FIG. 8 is an enlarged environmental cross sectional detail view of an impression coping and an implant located in bone tissue within the mouth of a patient, shown in representative proximity to the component shown in FIG. 2.

A representative maxillary impression 154 is shown in FIG. 8. Implant 152 is set in bone tissue 156 and an impression coping 158 is secured to implant 152 by a screw 160. Ball headed screw 100, which has been installed in bone tissue 156, is seen with its seat 120 and cap 126. Impression 154 has two molded layers 162, 166. An inner layer 162 abuts gum tissue 164, and is formed from a resilient dental impression material. Rigid, outer layer 166 is formed from a hardenable substance such as light cured acrylic material. Layer 162 is sufficiently resilient as to accommodate maneuvering of impression 154. Layer 162 also serves as a protective thermal barrier which shields gum tissue 164 from exothermic curing of the acrylic. Again, ball headed screw 100 is removed from the patient and from impression 154. When screws 100 (and all other ball headed screws 102, 104, 106, 108, 110) and 160 are removed, impression 154 may be pulled free from the mouth. Seat 120 for ball headed screw 160 and impression coping 158 remain integral with impression 154.

A similar procedure is repeated to produce an impression (not shown) for the remaining (mandibular) arch. Ball headed screws 100, 102, 104, 106, 108, 110 are then removed, followed by removal of the maxillary and mandibular impressions from the mouth.

In summary, at this point, an impression index 150, a maxillary impression 154 and a mandibular impression (not shown) have been fabricated, and implants have been placed. Unless complications arise, the surgical phase of the procedure has now been completed in one surgical session.

Figure 9:
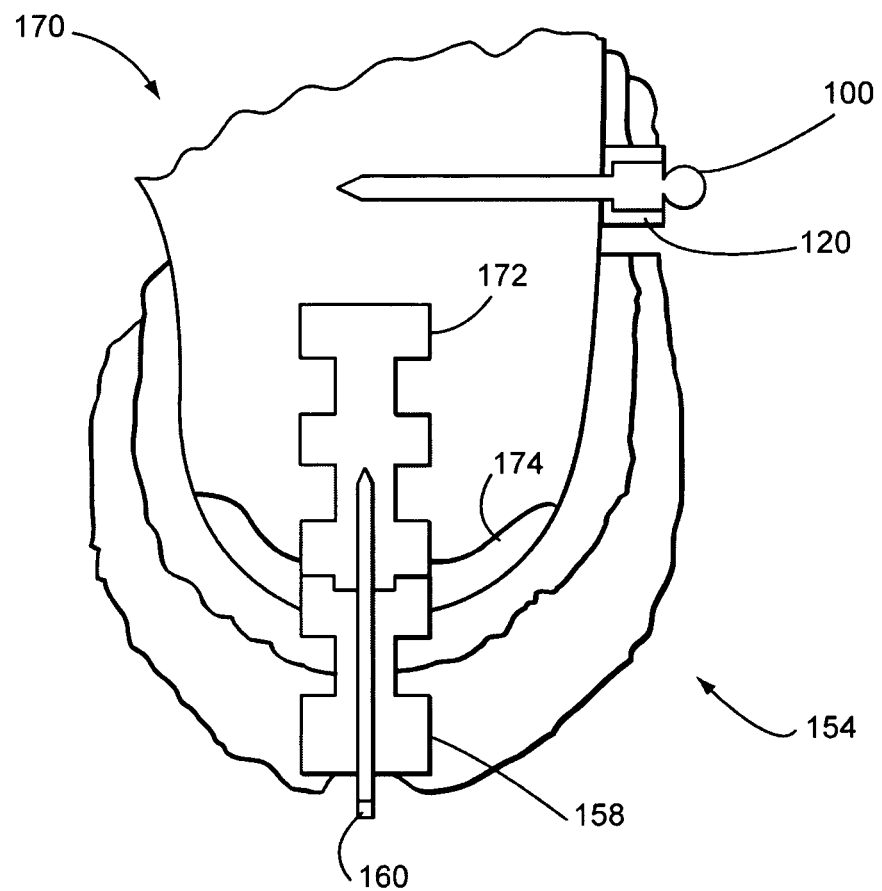
FIG. 9 is an enlarged environmental cross sectional detailed view of a built-up model of the anatomy shown in FIG. 8. This model is based on impressions of the actual anatomy.

In the laboratory where the prostheses are fabricated, master maxillary and mandibular casts are generated from their respective impressions, the fabrication of which impressions has just been described. Fabrication of a representative maxillary cast 170 is described, with reference to FIG. 9. Impression 154 serves as a mold in fabricating maxillary cast 170. An implant analog 172 oriented to its associated impression coping 158, and ball headed screw 100 inserted into seat 120 are cast integrally into maxillary cast 170. Preferably, a rubbery material 174 simulating gum is provided as part of maxillary cast 170. A corresponding mandibular cast (not shown) is made by a similar method, using the appropriate mandibular impression.

Fabrication of these two casts results in accurate replicas of the dental arch anatomy with ball headed screw 100 or an analog thereof, and implant analogs (e.g., 172) in place.

It may be desirable to stabilize the two casts having implant analogs against undesirable motion, such as torsion. This may be done for example by cross connecting coupled pairs of connector bars 128. Connector bars 128 may be provided with projections or texturing (neither shown) to better engage a cement.

Figure 10:
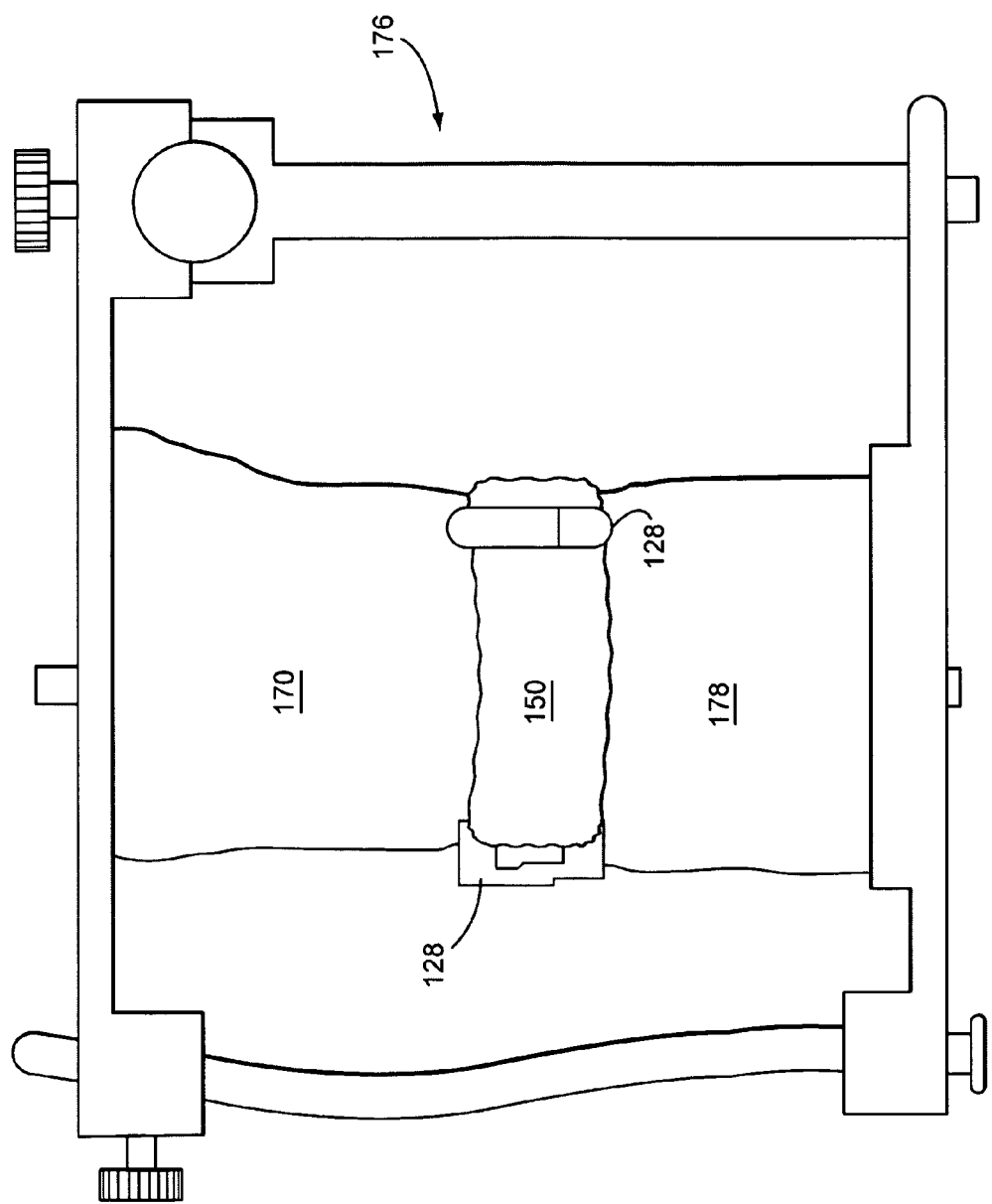
FIG. 10 shows the apparatus of FIG. 6 placed on a model of the mouth, with both the model and the apparatus of FIG. 6 held in an articulator to enable fine adjustments for assuring exact anatomical fidelity of prostheses based on these items.
Figure 11:
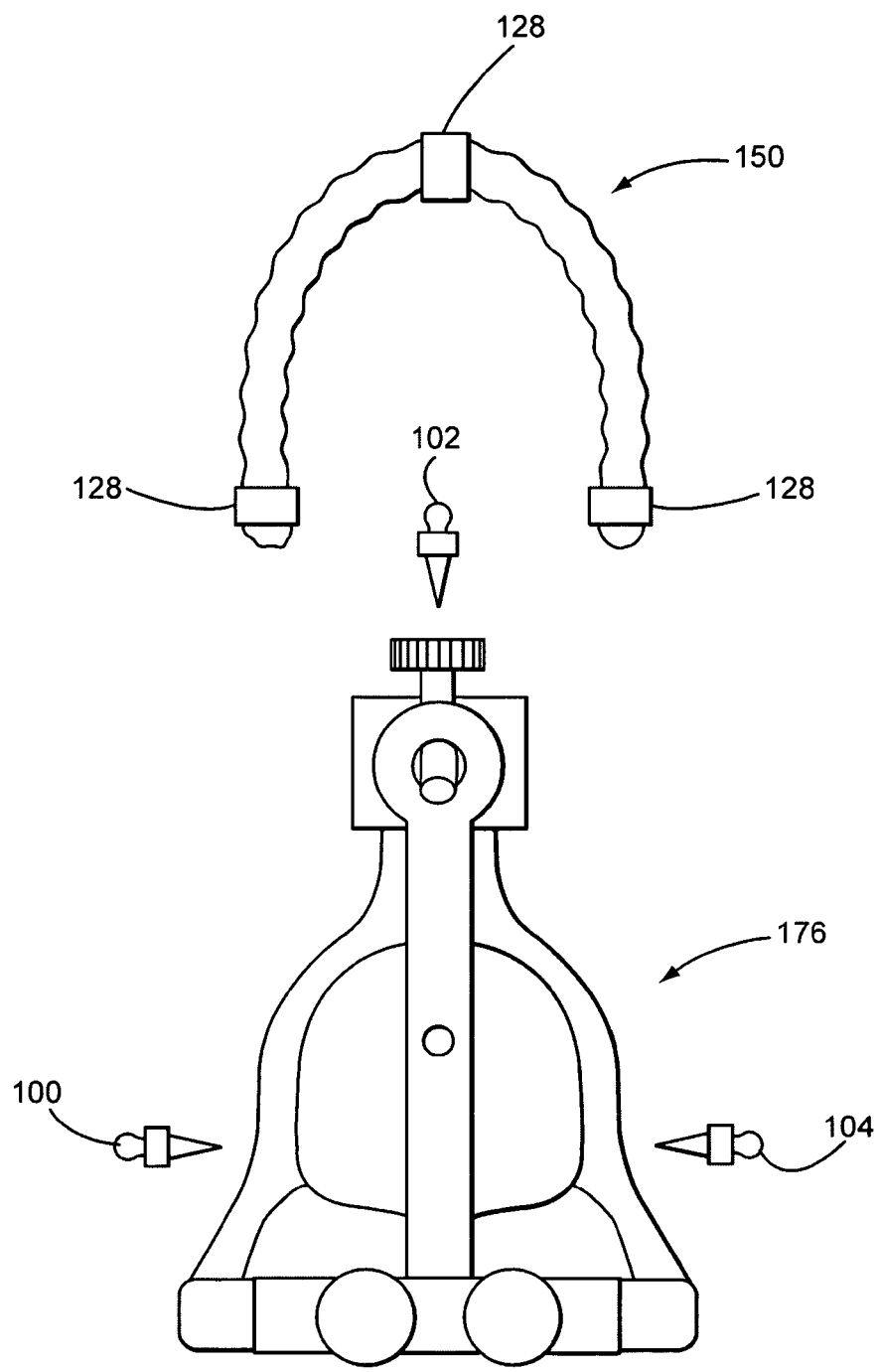
FIG. 11 is a partially exploded top plan view of the apparatus of FIG. 10.

Turning now to FIG. 10, maxillary cast 170 is mounted to a suitable articulator 176, and is positioned appropriately using face bow measurements before the maxillary impression is removed from that cast. With impressions removed therefrom, both maxillary and mandibular casts 170, 178 are mounted on articulator 176. Both articulators and the use thereof are believed to known to those of skill in the art. Consequently, neither articulators or the use thereof is further described herein. Impression index 150 is placed in articulator 176 to orient mandibular cast 178 properly with respect to maxillary cast 170. In so doing, sockets 134, 136 of connector bars 128 are mounted (e.g., by snap fitting) to spherical heads of the ball headed screw analogs (not separately shown in FIGS. 10 and 11) which are components of both casts 170, 178. Actual ball headed screws (e.g., 100, 102, 104, 106, 108, 110) may be used as analogs. Impressions are removed from the casts and a bite registration device (not shown) is attached. This establishes the master maxillary and mandibular casts 178, 170 properly oriented in three dimensions at the intended or planned or "as-desired" VDO.

Based on aligned casts 170, 178, temporary bridgework or even final prostheses may then be assembled in any desired manner and delivered to the patient for installation in the mouth.

This technique applies to both mechanically connected prostheses (e.g., using screws) and also to fastener and cement connected prostheses.

The invention includes both the described method as well as the apparatus used in the described procedure. For example, a kit of components for forming an impression index 150 (FIG. 6) for reproducing geometric relationships of the maxillary arch to the mandibular arch of a dental patient. Referring now again to FIGS. 2, 3, 4, 5 and 6, a kit of parts may comprise six ball headed screws 100 . . . 110 and three connector bars 128. Each ball headed screw 100 . . . 110 has a threaded shaft 112, an element such as hexagonal section 116 for turning or driving into bone tissue, and a spherical head or ball 118. Screws 100 . . . 110 preferably but not necessarily include base 114. Connector bars 128 each include two opposed sockets 134, 136 and a length adjusting and fixing mechanism. The length adjusting and fixing mechanism may take the form for example of forming connector bars in complementing sections 130, 132, each bearing a roughened surface such as texturing 142, and a suitable luting agent 133 for joining the two sections 130, 132. Preferably, the kit includes protective sleeves 126 and seats 120 for assisting in forming impressions.

The apparatus of the present invention also comprises an impression index 150, comprising three connector bars 128 which have been fixed in overall length at a selected dimension corresponding to the overall length of a connector 128 when one socket 134 engages one spherical head 118 of a ball headed screw 100, 102, 104, 106, 108, 110 which has been installed in the mouth of the patient, and a second socket 136 of the same connector bar 128 engages another spherical head 118 of a second ball headed screw 100, 102, 104, 106, 108, 110 when the second ball headed screw 100, 102, 104, 106, 108, 110 is installed in the mouth of the patient. In the impression index 150, the connector bars 128 are all connected together by impression material 144. Optionally, and where appropriate, impression index 150 includes six ball headed screws 100, 102, 104, 106, 108, 110 or analogs of screws 100, 102, 104, 106, 108, 110. The exaggerated depiction of impression index 150 is not literal, as the depiction of FIG. 6 does not show impressions of anatomical details that are actually captured, and does not reflect actual thickness of the impression material. Some aspects of impression index 150 may be better understood by examining FIG. 7. In FIG. 6, three connector bars 128 are shown indexed or releasably captured in impression material 144 in a position which captures the maxillary and mandibular relationships of the patient. FIG. 7 illustrates how ball headed screws 104, 110 establish location of connector bars 128.

Still referring to FIG. 7, it will be appreciated that because sockets 134, 136 are resilient, they snap fit to spherical heads 118 of ball headed screws 100, 102, 104, 106, 108, 110. Therefore, it is possible to remove connector bars 128 from impression material 144 and from engagement with ball headed screws 100, 102, 104, 106, 108, 110, and to be able to replace connector bars 128 within impression material 144.

Optionally, impression index 150 is reinforced or stiffened with cross members or the like (none shown) to prevent potential distortion of the captured relationships.

The connector bars 128 may take forms other than that described herein. Balls or spherical heads 118 may be replaced by snap fit structure other than partially spherical, or by still other types of attachable structure (none shown), such as threaded fasteners, deformable fasteners, clips, clamps, and still others known to those of skill in the art. It is presently contemplated that although partially spherical snap fit fasteners will prove the most convenient for dental practitioners, they are nonetheless not critical to the invention. Similarly, the manner in which connector bars are fixed to capture dimensions from one screw 110 . . . 118 to another screw 110 . . . 118 may be varied. Threaded fasteners, snap fit, welding (for example, ultrasonic welding of elastomeric materials), piercing with pins, friction fit, and other fastening techniques may be used.

Ball headed screws 100, 102, 104, 106, 108, 110 may omit base 114 if desired. The drive mechanism may vary from hexagonal section 116. For example, section 116 may be square or of any other non-circular configuration. Alternatively, a drive socket (not shown) may be formed in spherical head 118.

The invention applies to both mechanically connected and also to cemented prostheses.

It will be appreciated that while the invention has been described in terms of certain specific elements, it is nonetheless feasible that such elements may be replaced by others which provide equivalent function or structure. Most notably, ball headed screws 100, 102, 104, 106, 108, 110 previously referred to may take any suitable form. It is merely desired that members of adjustable length be provided to span and fix the distance between and orientation of their respective anchor members in the upper and lower jaws. In a similar vein, it is possible to utilize five or even four anchoring points in the mouth, with one or two points doing dual duty in that each is to be connected to two different anchoring points in the opposed jaw.

It would be possible to reduce the number of connector bars 128 by providing connector bar assemblies (not shown) which include more than one connector bar. For example, connector bar assemblies may be formed in the configuration of a "V" in which two connector bars terminate at a common socket. Other configurations include that of an "X" in which a monolithic or pivotally connected pair of crossing connector bars span diagonally rather than vertically adjacent ball headed screws. Still further configurations such as for example curved, irregularly configured, and "W" shaped configurations could be utilized to reduce the number of physically separate and distinct connector bars to the same effect.

It would be possible that in some cases, ball headed screws 100 . . . 110 or their equivalents may be left in place to serve therapeutic procedures which are to be performed subsequently to a first therapeutic procedure.

In a further embodiment (not shown), it would be possible to replace moldable material which becomes impression index 150 with a flexible, plate-like member (not shown) bearing a plurality of sockets to be maneuvered into position over the spherical heads of the screws or of other reference markers. The flexible member would then be rendered rigid, such as for example by encasing it fully or partly with a material which is rigid when cured.

It is also possible to reduce the number of anchoring points and spanning members (e.g., connector bars 128) by employing some of these elements to do dual duty. That is, for example, one anchoring point in the upper jaw may be connected by different spanning members to two different anchoring points in the lower jaw.

Where there is one or more pre-existing implants (not shown), it would be possible to adapt a connector bar 128 or even the entire apparatus to secure to the pre-existing implant or implants, as opposed to installing a ball headed screw 100, 102, 104, 106, 108, 110 in bone tissue.

Where the invention is provided as a kit, the kit may include extra or redundant components, components of alternative forms, for example to increase convenience of the dental practitioner, or, where one component has been designed to provide the function of more than one component as described herein, may include fewer than six ball headed screws 110 . . . 118 and may include fewer than three connector bars 128.

It would also be possible to combine the concepts of compound or joined connector bars with dual duty anchoring points.

It will also be understood that the order of steps of the work done on maxillary and mandibular arches, and in other areas of the procedure, may be changed or reversed from the order described herein, at the discretion of the dental practitioner.

It is contemplated that any known three dimensional imaging method could be employed to facilitate locating and guiding of optimal locations and placement of both implants and of ball headed screws 100, 102, 104, 106, 108, 110.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

I claim:

1. A method for capturing and preserving three dimensional orientation of the jaws of a patient requiring dental restoration in both the maxillary and mandibular arches, the method enabling restoration of both the maxillary and the mandibular arches pursuant to a single surgery, the steps comprising:
    a) in a patient having jaws comprising a maxillary arch and a mandibular arch, establishing at least three pairs of reference points in said maxillary and said mandibular arches, each of said at least three pairs of reference points comprising a maxillary reference point in said maxillary arch and a corresponding mandibular reference point in said mandibular arch;
    b) installing an apparatus interconnecting said maxillary reference point and said mandibular reference point of each of said at least three pairs of reference points, thereby capturing a planned vertical dimension of occlusion;
    c) fabricating an index against at least a portion of said apparatus capturing at least said planned vertical dimension of occlusion and said at least three pairs of reference points and indicating the planned plane of occlusion before surgery;
    d) placing at least one dental implant in each of said maxillary and said mandibular arch;
    e) after said placing step (d) forming an impression of each of said maxillary and said mandibular arch, said impressions capturing the positions of the implants, at least a portion of said apparatus, and the contiguous hard and soft tissues within said arches;
    wherein each of said establishing (a), said installing step (b), said fabricating step (c), said placing step (d,) and said forming step (e) are performed in a single surgical session; and
    f) using said formed impression of each of said maxillary and said mandibular arch in conjunction with said apparatus and said index to generate casts of said maxillary and mandibular arches and to accurately orient said casts in an articulator to enable fabrication of dental prostheses for each of said maxillary and said mandibular arch incorporating said planned vertical dimension of occlusion.

2. The method for capturing and preserving three dimensional orientation of the jaws of a patient as recited in claim 1, wherein said establishing step (a) comprises the sub-steps:
    i) placing at least a first maxillary reference marker, a second maxillary reference marker, and a third maxillary reference marker in said maxillary arch;
    ii) placing at least a first mandibular reference marker, a second mandibular reference marker, and a third mandibular reference marker in said mandibular arch; and
    wherein said installing an apparatus step (b) comprises connecting each of said first, second, and third maxillary reference markers to a corresponding one of said first, second, and third mandibular reference markers with a respective first, second, and third connector bar.

3. The method for capturing and preserving three dimensional orientation of the jaws of a patient as recited in claim 2, wherein said fabricating an index step (c) comprises fabricating an index that captures the respective positions of said first connector bar, said second connector bar, and said third connector bar.

4. The method for capturing and preserving three dimensional orientation of the jaws of a patient as recited in claim 2, wherein said maxillary and said mandibular reference markers comprise ball headed screws, and wherein said placing sub-step (i) of maxillary reference markers comprises placing a first ball headed screw in a first position anchored in maxillary bone tissue, a second ball headed screw in a second position anchored in maxillary bone tissue, and a third ball headed screw in a third position anchored in maxillary bone tissue, and said sub-step (ii) of mandibular reference markers comprises placing a fourth ball headed screw in a first position anchored in mandibular bone tissue, placing a fifth ball headed screw in a second position anchored in mandibular bone tissue, and placing a sixth ball headed screw in a third position anchored in mandibular bone tissue.

5. The method for capturing and preserving three dimensional orientation of the jaws of a patient as recited in claim 4 wherein said installing an apparatus step (b) comprises providing said first connector bar with a first socket for engagement with said ball head of said first ball headed screw and a second socket for engagement with said ball head of said fourth ball headed screw, providing said second connector bar with a first socket for engagement with said ball head of said second ball headed screw and a second socket for engagement with said ball head of said fifth ball headed screw, and providing said third connector bar with a first socket for engagement with said ball head of said third ball headed screw and a second socket for engagement with said ball head of said sixth ball headed screw.

6. The method for capturing and preserving three dimensional orientation of the jaws of a patient as recited in claim 2, wherein each of said first, second, and third connector bars comprise a length adjusting mechanism and said installing an apparatus step (b) comprises adjusting the length of at least one of said first, second, and third connector bars.

7. The method for capturing and preserving three dimensional orientation of the jaws of a patient as recited in claim 4 wherein said forming an impression step (e) comprises the sub-steps:
i) fabricating a maxillary impression using dental impression material to capture impressions of the at least one implant, of said first, second and third ball headed screws, and said maxillary arch; and
ii) fabricating a mandibular impression using dental impression material to capture impressions of the at least one implant, of said fourth, fifth, and sixth ball headed screws, and said mandibular arch.

8. The method for capturing and preserving three dimensional orientation of the jaws of a patient as recited in claim 7 wherein said forming an impression step (e) further comprises the sub-step:
iii) making face bow measurements on said maxillary arch with said maxillary impression in place on the mouth.

9. The method for capturing and preserving three dimensional orientation of the jaws of a patient as recited in claim 1, the steps further comprising:
g) obtaining at least one selected from the group: a ball headed screw, a connector bar comprising a first socket adapted to removably engage a head of a first ball headed screw and an opposed second socket adapted to engage a head of another ball headed screw, and a cap adapted to resiliently and removably engage said head of a ball headed screw.

10. The method for capturing and preserving three dimensional orientation of the jaws of a patient as recited in claim 9, wherein said obtaining step (g) comprises obtaining at least a connector bar comprising a length adjustment mechanism capable of fixing overall length of said connector bar at a selected dimension.

11. The method for capturing and preserving three dimensional orientation of the jaws of a patient as recited in claim 10, wherein said obtaining step (g) comprises obtaining a kit of parts comprising at least a ball headed screw and the connector bar.

12. The method for capturing and preserving three dimensional orientation of the jaws of a patient as recited in claim 11, wherein said kit of parts further comprises a cap adapted to resiliently and removably engage said head of a ball headed screw.

13. The method for capturing and preserving three dimensional orientation of the jaws of a patient as recited in claim 11, wherein said said kit of parts further comprises at least six ball headed screw and three connector bars.

14. The method for capturing and preserving three dimensional orientation of the jaws of a patient as recited in claim 13, wherein said obtaining step (g) comprises obtaining a kit of parts further comprises obtaining at least six caps, each adapted to resiliently and removably engage said head of a ball headed screw.

* * * * *